(12) United States Patent
Maier et al.

(10) Patent No.: US 7,091,368 B2
(45) Date of Patent: Aug. 15, 2006

(54) METHOD FOR THE PURIFICATION OF LIPONIC ACID

(75) Inventors: Ulrike Maier, Mannheim (DE); Martin Jochen Klatt, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/532,205

(22) PCT Filed: Nov. 17, 2003

(86) PCT No.: PCT/EP03/12819

§ 371 (c)(1),
(2), (4) Date: Apr. 22, 2005

(87) PCT Pub. No.: WO2004/048362

PCT Pub. Date: Jun. 10, 2004

(65) Prior Publication Data

US 2006/0014823 A1    Jan. 19, 2006

(30) Foreign Application Priority Data

Nov. 26, 2002   (DE) ............... 102 55 242

(51) Int. Cl.
*C11B 3/10*     (2006.01)
(52) U.S. Cl. .................... 554/193; 554/191
(58) Field of Classification Search ........... 554/193, 554/191
See application file for complete search history.

(56) References Cited

FOREIGN PATENT DOCUMENTS

| DE | 100 22 856 | 11/2001 |
|---|---|---|
| DE | 100 27 875 | 12/2001 |
| DE | 100 44 000 | 3/2002 |
| EP | 0 487 986 | 6/1992 |
| EP | 0 543 088 | 5/1993 |
| JP | 35704-60 | 5/1960 |
| WO | 02/044163 | 6/2002 |

OTHER PUBLICATIONS

Nakata. "Biologically active lipoic-acid-like substances in urine. II. Purification and chemical properties", Chemical Abstracts, vol. 71, No. 25, p. 24, 119752c 1969.

Bringmann et al. "A Short and Productive Synthesis of (R)-alpha-Lipoic Acid", Z. Naturforsch., vol. 54b. pp. 655-661 1999.

Adger et al. "The Synthetis of (R)-(+)-Lipoic Acid using a Monooxygenase-Catalysed Biotransformation as the Key Step", Bioorganic & Medicinal Chemistry, vol. 5, pp. 253-261 1997.

Yadav et al. "Synthesis of alpha-lipoic acid- A highly useful biologically active compound", Journal of Scientific & Industrial Research, vol. 49, pp. 400-409 1990.

Gopalan et al. "Stereochemical Control of Yeast Reductions: Synthesis of R-(+)-alpha-Lipoic Acid", Tetrahedron Letters, vol. 30, pp. 5705-5708 1989.

Brookes et al. "Proof that the Absolute Configuration of Natural alpha-Lipoic Acid is R by the Synthesis of its Enantiomer [(S)-(−)-alpha-Lipoic acid] from (S)-Malic Acid", J. Chem. Soc., Chem. Commun., pp. 1051-1053 1983.

*Primary Examiner*—Deborah D. Carr
(74) *Attorney, Agent, or Firm*—Oblon, Spivak, McClelland, Maier & Neustadt, P.C.

(57) ABSTRACT

The invention relates to a process for purifying lipoic acid, which comprises adding to a solution of lipoic acid at least 0.1 times the amount of an adsorbent, based on the mass of lipoic acid to be purified, and subsequently removing the adsorbent. It is possible in this way to provide racemic or nonracemic lipoic acid with an oligomer content below 1% by weight, for example from 0.1 to 1% by weight.

8 Claims, No Drawings

METHOD FOR THE PURIFICATION OF LIPONIC ACID

The present invention relates to a process for purifying racemic or nonracemic lipoic acid. In particular, the invention relates to a process for purifying R- or S-lipoic acid which has an oligomer content in the range from about 0.1 to about 1.0% by weight.

The invention further relates to the use of the lipoic acid purified in the manner according to the invention in drugs, cosmetics and food products.

Dihydrolipoic acid and lipoic acid are naturally occurring substances having particular importance in cellular metabolism. R-Lipoic acid plays a central part in energy generation as coenzyme, e.g. pyruvate dehydrogenase. R-Lipoic acid is activated, in order to display fully its very good antioxidant properties, to dihydrolipoic acid in metabolism. Dihydrolipoic acid and lipoic acid can, because they are interconverted in vivo, be used for the same areas of application. R-Lipoic acid has an advantageous effect on age-related changes in metabolism and is therefore also of interest in the cosmetic sector.

Lipoic acid and dihydrolipoic acid can be employed as nutraceuticals in the food product sector. The use of dihydrolipoic acid and/or lipoic acid as drug is also possible. For example, it is known that R-lipoic acid increases insulin sensitivity and thus can be used as antidiabetic, and for preventing and alleviating late damage from diabetes. In addition, lipoic acid or dihydrolipoic acid or derivatives thereof can be employed for the treatment of disorders of glucose metabolism (e.g. in the CNS), for insulin resistance, cancer and hearing defects.

Numerous methods for preparing optically pure R- and S-lipoic acid and dihydrolipoic acid are known from the literature (G. Bringmann, D. Herzberg, G. Adam, F. Balkenhohl, J. Paust, Z. Naturforschung 1999, 54b, 665–661; B. Adger et al., Bioorg. Med. Chem. 1997, 5, 253–61; J. S. Yadav, S. Mysorekar, K. Garyali, J. Scientific & Industrial Res. 1990, 49, 400–409; A. S. Gopalan, H. K. Jacobs, Tetrahedron Lett 1989, 42, 5705; M. H. Brookes, B. T. Golding, A. T. Hudson, Perkin Transaction I, 1988, 9–12; M. H. Brookes, B. T. Golding, D. A. Howes, A. T. Hudson, Chemical Communication 1983, 1051–53; JP 1960-35704; EP-A-543088; EP-A-487 986; DE-A-100 44 000 and DE-A-100 59 718).

Since lipoic acid and dihydrolipoic acid are also intended to be used in humans, products of maximal purity are desired, and simple and economic production thereof in large quantities must be ensured.

It is to be regarded as particularly problematic in this connection that the lipoic acid obtained is contaminated by characteristic impurities resulting from oligomerization or polymerization of lipoic acid itself. Even small quantities of these oligomers in the product lead to serious complications during further processing and cannot be tolerated in relation to a pharmaceutical use of the lipoic acid produced in this way.

DE-A-100 44 000 and DE-A-100 59 718 describe a clarifying filtration process for purifying lipoic acid obtained by oxidation of dihydrolipoic acid, which is suitable for experiments on a laboratory scale.

Industrial production of lipoic acid with oligomer contents of less than 1.0% by weight by contrast presents a problem which has not yet been satisfactorily solved.

It is an object of the present invention to develop a process for purifying lipoic acid which can also be applied economically on the industrial scale.

We have found that this object is achieved by a process for purifying lipoic acid, which comprises adding to a solution of lipoic acid at least 0.1 times the amount of an adsorbent, based on the mass of lipoic acid to be purified, and subsequently removing the adsorbent. It is possible in this way to provide racemic or nonracemic lipoic acid with an oligomer content of less than 1% by weight, for example from 0.1 to 1% by weight.

Solvents suitable for producing solutions for the lipoic acid purification process of the invention are organic solvents of low polarity, especially aliphatic, where appropriate heteroatom-substituted hydrocarbons having from one to twelve carbon atoms, such as, for example, pentane, hexane, cyclohexane, heptane or dichloroethane or aromatic, where appropriate alkyl- or heteroatom-substituted hydrocarbons such as toluene, ethylbenzene or chlorobenzene or mixtures of said solvent classes.

Preferred solvents for the purification process of the invention are aliphatic hydrocarbons having from one to twelve carbon atoms and alkyl-substituted aromatic hydrocarbons having up to twelve carbon atoms.

Particularly preferred solvents are pentane, hexane, cyclohexane, heptane, octane, toluene and ethylbenzene, very particularly preferably heptane and toluene or mixtures of at least two of said solvents.

Suitable adsorbents are commercially available adsorbents such as silica gels, neutral aluminas, basic aluminas and mixtures of said adsorbents, preferably silica gels.

Particularly preferred adsorbents are silica gel 60 having a particle size of 0.04–0.063 mm, silica gel 40 (particle size 0.015–0.035 mm) and silica gel 100 (particle size 0.063–0.2 mm).

The quantity of the adsorbent to be employed in the purification process of the invention depends on the quantity of lipoic acid to be purified and is generally at least 10% of the quantity by weight of the lipoic acid to be purified. This applies in particular on the use of the particularly preferred adsorbent silica gel. It is particularly preferred in this connection to use at least 15% by weight silica gel based on the quantity of lipoic acid to be purified. It is very particularly preferred to use from 20 to 50% by weight silica gel based on the quantity of lipoic acid to be purified.

Separation processes suitable for removing the adsorbent are all those which appear suitable to the skilled worker. It is particularly suitable to carry out a filtration to remove the silica gel which is particularly preferably employed as adsorbent.

The process of the invention is suitable for purifying racemic and nonracemic lipoic acid. Nonracemic lipoic acid means in this connection all mixtures of R- and S-lipoic acid in which the two enantiomers are not present in equal parts.

However, the process of the invention is preferably used to purify R- or S-lipoic acid having an enantiomeric excess (ee) of in each case above 80% ee, particularly preferably above 90% ee, very particularly preferably above 95% ee. It is most preferred to purify R- or S-lipoic acid having an enantiomeric excess of in each case above 99% ee. The purification process of the invention is suitable for producing chemically pure R- and S-lipoic acid. It is particularly suitable for producing R- or S-lipoic acid having a chemical purity of at least 99%, very especially at least 99.5%. It is particularly suitable for producing R- or S-lipoic acid having a maximum content of 0.5% by weight of the lipoic acid oligomers which are problematic as impurities. The purification process of the invention is very particularly suitable for producing R- or S-lipoic acid having an oligomer content not exceeding 0.2% by weight.

The lipoic acid to be purified can be prepurified or be employed as solid or partially dissolved crude product of a preceding process step in the purification process of the invention. The purification process can be carried out on any scale. It is particularly suitable, however, for purifying lipoic acid on the industrial scale.

In addition to the process for purifying lipoic acid, the invention also relates to the further processing of the R- or S-lipoic acid purified according to the invention, e.g. into pharmacologically acceptable salts such as alkali metal and alkaline earth metal salts or, for example, the trometamol salt (International nonproprietary name for tris(hydroxymethyl)aminomethane) of R-lipoic acid.

The invention additionally relates also to the use of racemic and nonracemic or enantiopure lipoic acid purified by the process of the invention in drugs or in cosmetics or in food products, for example as nutraceutical. This includes the formulation of racemic or nonracemic lipoic acid purified in the manner of the invention, especially of R- or S-lipoic acid purified according to the invention in a pharmacologically or dermatologically acceptable form.

In relation to the diverse possibilities for formulating and using lipoic acid, reference may be made by way of example to the contents of DE-A-100 22 856 and of DE-A-100 27 875 (PCT/EP/01/06385).

The following examples serve to illustrate the invention without, however, restricting it:

EXEMPLARY EMBODIMENT 25.3 kg (250 mol) of triethylamine and 20 kg (100 mol) of methyl (6S)-6,8-dihydroxyoctanoate were introduced into 300 liters of toluene and, while cooling, 28.6 kg (250 mol) of methanesulfonyl chloride were metered in. After removal of the triethylammonium hydrochloride, most of the solvent was distilled out.

A methanolic solution of 50.7 kg of sodium sulfide and 14.4 kg of sulfur was then added. After the reaction was complete, the mixture was diluted with water, and 40 kg of a 12% strength solution of $NaBH_4$ in 14 M NaOH (Borol solution) were added. Part of the solvent mixture was distilled out, and the remaining reaction mixture was adjusted to pH 4 with sulfuric acid and then extracted with toluene. The organic phase was adjusted to pH 9 and extracted with toluene.

The R-dihydrolipoic acid isolated in this way was taken up in water and, after addition of a catalytic quantity of iron(II) sulfate, aerated until reaction was complete. This was followed by acidification (pH 2) with sulfuric acid and extraction with toluene. The toluene solution was mixed with heptane and forced through a pressure filter packed with 5 kg of silica gel 60 under slightly elevated pressure.

The filtered solution was cooled and the R-lipoic acid which crystallized out was isolated by pressure filtration and dried in a stream of nitrogen.

R-Lipoic acid (ee>99.9%) was obtained in a yield of 73% of theory based on methyl (6S)-6,8-dihydroxyoctanoate. The content of lipoic acid oligomers was determined by gel permeation chromatography (column: PL gel, eluent THF) to be 0.3%.

COMPARATIVE EXAMPLE

The abovementioned example was repeated under the same conditions apart from the purification step. The toluene solution obtained after acidification with sulfuric acid was mixed with heptane and forced through a pressure filter packed with 1 kg of silica gel 60 under slightly elevated pressure.

The filtered solution was cooled and the R-lipoic acid which crystallized out was isolated by pressure filtration and dried in a stream of nitrogen.

R-Lipoic acid (ee>99.9%) was obtained in a yield of 73% of theory based on methyl (6S)-6,8-dihydroxyoctanoate. The content of lipoic acid oligomers was determined by gel permeation chromatography (column: PL gel, eluent THF) to be 2.5%.

We claim:

1. A process for purifying lipoic acid, which comprises adding to a solution of lipoic acid at least 0.1 times the amount of an adsorbent, based on the mass of lipoic acid to be purified, and subsequently removing the adsorbent.

2. The process as claimed in claim 1, wherein the lipoic acid to be purified has been obtained by oxidation of dihydrolipoic acid.

3. The process as claimed in claim 1, wherein at least 0.2 to 0.5 times the amount of an adsorbent, based on the mass of lipoic acid to be purified, is used.

4. The process as claimed in claim 1, wherein the silica gel is used as adsorbent.

5. The process as claimed in claim 1, wherein the lipoic acid to be purified is dissolved in an organic solvent or in a mixture of at least two organic solvents.

6. The process as claimed in claim 1, wherein the lipoic acid is dissolved in heptane or toluene or a mixture of these solvents.

7. The process as claimed in claim 1, wherein racemic or nonracemic lipoic acid is employed as lipoic acid.

8. A drug, cosmetic, or food product comprising purified lipoic acid obtained by the process as claimed in claim 1.

* * * * *